(12) United States Patent
Mannion et al.

(10) Patent No.: US 9,683,958 B2
(45) Date of Patent: Jun. 20, 2017

(54) NANOFLUIDIC DEVICE FOR CHARGE ANALYSIS OF STRAIGHTENED MOLECULES

(71) Applicant: Agilent Technologies, Inc., Loveland, CO (US)

(72) Inventors: John Mannion, Palo Alto, CA (US); Bo Curry, Redwood City, CA (US); Brian Jon Peter, Los Altos, CA (US)

(73) Assignee: Agilent Technologies, Inc., Santa Clara, CA (US)

( * ) Notice: Subject to any disclaimer, the term of this patent is extended or adjusted under 35 U.S.C. 154(b) by 192 days.

(21) Appl. No.: 14/482,803

(22) Filed: Sep. 10, 2014

(65) Prior Publication Data

US 2015/0068901 A1   Mar. 12, 2015

Related U.S. Application Data

(60) Provisional application No. 61/876,667, filed on Sep. 11, 2013.

(51) Int. Cl.
   *G01N 27/414*   (2006.01)
   *G01N 27/447*   (2006.01)

(52) U.S. Cl.
   CPC ..... *G01N 27/4145* (2013.01); *G01N 27/4473* (2013.01)

(58) Field of Classification Search
   CPC ........... G01N 27/4145; G01N 27/4473; G01N 33/48721; G01N 27/414; G01N 27/44791; B82Y 30/00; B01L 3/502761; B01L 2300/0896; B01L 2400/0487; B01L 2400/0421; B01L 2300/0645; B01L 2200/0663; C12Q 1/6869
   See application file for complete search history.

(56) References Cited

U.S. PATENT DOCUMENTS

| | | | |
|---|---|---|---|
| 7,223,540 B2 | 5/2007 | Pourmand et al. |
| 7,785,785 B2 | 8/2010 | Pourmand et al. |
| 7,932,034 B2 | 4/2011 | Esfandyarpour et al. |
| 8,012,756 B2 | 9/2011 | Pourmand et al. |
| 8,313,907 B2 | 11/2012 | Pourmand et al. |

(Continued)

FOREIGN PATENT DOCUMENTS

WO   WO2010044932   4/2010

OTHER PUBLICATIONS

Eid, et al., "Real-Time DNA Sequencing from Single Polymerase Molecules", Science, 2009, vol. 323, No. 5910 pp. 133-138.

(Continued)

*Primary Examiner* — Xiuyu Tai

(57) ABSTRACT

This disclosure provides, among other things, a nanofluidic device sensing device is provided. In certain embodiments, the device contains: a) a channel comprising a floor and a ceiling, b) an array of charge sensors in the floor and/or ceiling of the channel, arranged along the longitudinal axis of the channel; c) a capture area in the floor and/or ceiling of the channel at the entrance end of the channel; and d) a first electrode and a second electrode, wherein the first and second electrodes are positioned to provide an electrophoretic force along the longitudinal axis of the channel. Other embodiments, e.g., methods, are also described.

12 Claims, 8 Drawing Sheets

(56) References Cited

U.S. PATENT DOCUMENTS

2006/0275778 A1* 12/2006 Wu .................. G01N 33/48721
                                                       435/6.11
2013/0165328 A1*  6/2013 Previte ................ C12Q 1/6874
                                                         506/2
2013/0252235 A1*  9/2013 Tang .................... C12Q 1/6869
                                                        435/6.1

OTHER PUBLICATIONS

Mann Ion, et al., "Conformational Analysis of Single DNA Molecules Undergoing Entropically Induced Motion in Nanochannels", Biophysical Journal vol. 90 Jun. 2006 4538-4545.
Rothberg, et al., "An integrated semiconductor device enabling non-optical genome sequencing", Nature 475, 348-352.
Tegenfeldt, et al., "The dynamics of genomic-length DNA molecules in 100-nm channels", PNAS, vol. 101, No. 30, 2004.

* cited by examiner

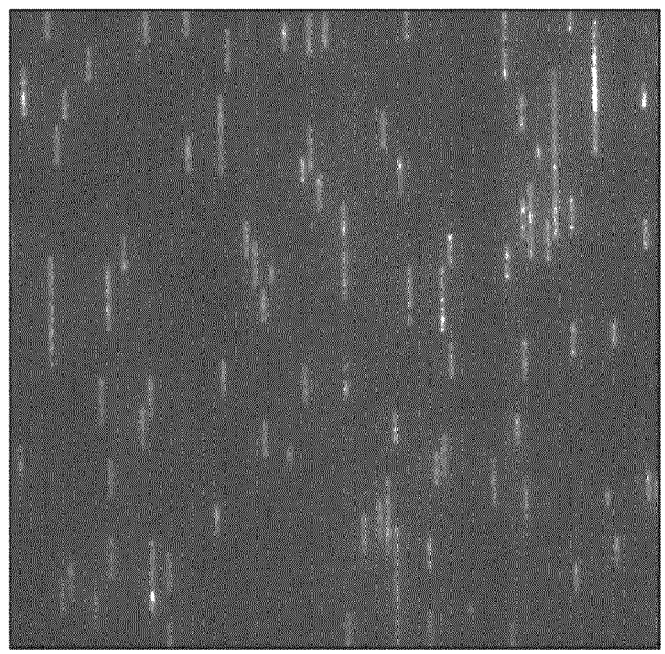
c)
8 μm extension, 48.5 kb molecule
1000 nm
DNA Molecule Floating in Free Solution
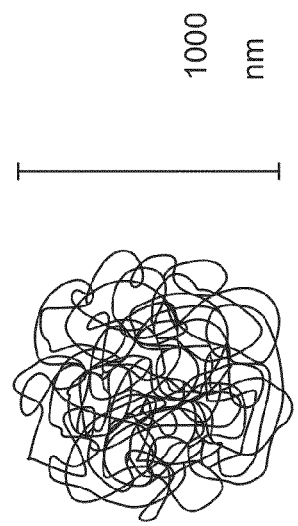
DNA Molecule in a Nanochannel
100 nm
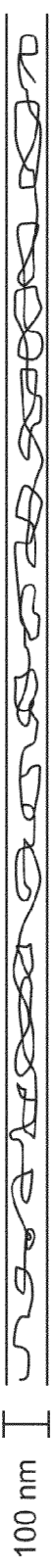
a)
b)
FIG. 9

NANOFLUIDIC DEVICE FOR CHARGE ANALYSIS OF STRAIGHTENED MOLECULES

CROSS-REFERENCING

This application claims the benefit of U.S. Provisional Application Ser. No. 61/876,667, filed on Sep. 11, 2013, which application is incorporated by reference herein.

BACKGROUND

Methods by which biologically-relevant entities such as nucleic acids can be analyzed directly can potentially outperform conventional methods because direct methods are faster, more accurate and more sensitive. Nanofluidic systems present new possibilities for direct analysis of biomolecules, thereby providing new ways to analyze biological molecules.

SUMMARY

This disclosure provides, among other things, a nanofluidic device sensing device is provided. In certain embodiments, the device contains: a) a channel comprising a floor and a ceiling, b) an array of charge sensors in the floor and/or ceiling of the channel, arranged along the longitudinal axis of the channel; c) a capture area in the floor and/or ceiling of the channel at the entrance end of the channel; and d) a first electrode and a second electrode, wherein the first and second electrode are positioned to provide an electrophoretic force along the longitudinal axis of the channel.

Other embodiments, including methods, are also described. Further embodiments would be apparent to people of skill in the art.

BRIEF DESCRIPTION OF THE FIGURES

The skilled artisan will understand that the drawings, described below, are for illustration purposes only. The drawings are not intended to limit the scope of the present teachings in any way.

FIG. 9 schematically illustrates a) long double stranded DNA molecule floating in free solution assumes a roughly spherical conformation. b) the same molecule loaded into a nanochannel will elongate along the nanochannel axis due to self-avoidance. c) fluorescent videomicroscopy frame showing a number of DNA molecules in elongated equilibrium states in an array of nanochannels.

DESCRIPTION

Figure 1:
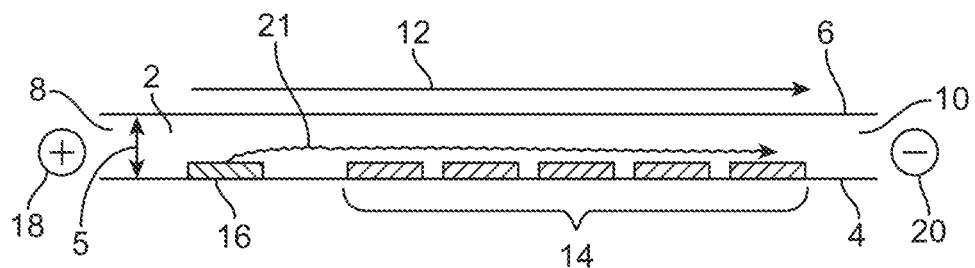
FIG. 1 schematically illustrates a subject nanofluidic device sensing device, shown from the side.

Before the present invention is described in greater detail, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, representative illustrative methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

A "channel" references an enclosed, elongated, volume having a floor, ceiling and walls, which is accessible via an entrance and/or an exit.

It will also be appreciated that throughout the present application, that words such as "top", "upper", "lower", "floor" and "ceiling" are used in a relative sense only.

A nanofluidic device sensing device is provided. With reference to FIG. 1, in certain embodiments, the device comprises: a channel 2 comprising an opposing floor 4 and ceiling 6, wherein the floor and the ceiling are spaced by a distance 5 of less than 1 µm (e.g., 500 nm or less, 100 nm or less, 50 nm or less, 20 nm or less or 10 nm or less). As shown, channel 8 comprises an entrance end 8 and an exit end 10 that define the longitudinal axis of the channel (shown by arrow 12). The device contains an array of charge sensors 14 (e.g., ion sensitive field effect transistors) in the floor and/or ceiling of the channel, arranged along the longitudinal axis of the channel. As shown, the charge sensors are in the floor of the device. In other embodiments they charge sensors may be in the ceiling or the floor and ceiling of the device. The device additionally contains a capture area 16 in the floor and/or ceiling of the channel at the entrance end of the channel, wherein the capture area comprises surface exposed groups that bind to or react with and end of a functionalized nucleic acid molecule. In FIG. 1, the capture area is shown as being in the floor of the device. The capture area can also be in the ceiling of the device. The device additionally comprises first electrode 18 and second electrode 20, wherein the first and second electrodes are positioned to provide an electrophoretic force along the longitudinal axis of the channel. This electrophoretic force is sufficient to cause straightening of a nucleic acid molecule 21 that is attached to the capture area. The straightening of nucleic acid molecule 21 places a region of interest of the nucleic acid molecule in proximity with a plurality of the charge sensors 14.

The length and width of the channel 2 may vary widely. In certain cases, the length and width of channel 2 may be, independently, channel is up to 100 µm in length, e.g., up to 50 µm in length, up to 10 µm in length or up to up to 5 µm in length, although longer or wider channels may be used in some applications.

In certain embodiments, the entrance end and an exit end of the channel are adapted for connection with a source of reagents and a waste line, respectively. In these embodiments, the ends of the channel may be adapted to connect to a microfluidic system for dispensing reagents and removing waste, e.g., via a screw fit, compression fit or another type of liquid-tight connector.

In particular embodiments, the channel is not linear along its longitudinal axis and, in certain embodiments, the longitudinal axis may be curved or stepped such that, with reference to FIG. 1, the straightened nucleic acid molecule is closer to the charge sensors than if the channel is straight.

The number of charge sensors in the device and their spacing may also vary greatly. In particular embodiments, there may be at least 5, at least 10, at least 50 or at least 100 charge sensors in a subject device, all arranged along the longitudinal axis of the channel. On any one surface (e.g., the floor or ceiling), the charge sensors should be spaced by a minimal distance (e.g., by less than 100 nm, less than 10 nm, or less than 1 nm). In certain cases, any gaps between the sensors can be filled by placing a sensor that covers a gap on the opposite surface. In particular embodiments, the device may comprise a plurality of nanofluidic diodes, wherein the diodes divide the channel into multiple segments with different surface charges.

The surface exposed groups in capture area 16 bind to or react with a functionalized nucleic acid molecule, e.g., a site towards an end, e.g., the 5' or 3' end of a functionalized nucleic acid molecule. Nucleic acid molecules can be attached to the capture area via any convenient method. In some cases, a functionalized nucleic acid molecule may be attached non-covalently to capture area 16 via a high-affinity covalent interaction such as that between a biotin moiety (which term includes biotin and biotin analogue such as desthiobiotin, oxybiotin, 2'-iminobiotin, diaminobiotin, biotin sulfoxide, biocytin, etc.) and streptavidin. In other embodiments, a functionalized nucleic acid molecule can be attached to the capture area via a reaction that forms a covalent bond, e.g., a reaction between an amine group in a lysine residue of a protein or an aminated oligonucleotide with an NHS ester to produce an amide bond, or a reaction between a sulfhydryl group in a cysteine residue of a protein or a sulfhydrl-oligonucleotide with a sulfhydryl-reactive maleimide on the capture area. Protocols for linking capture agents to various reactive groups are well known in the art. In certain cases, the surface exposed groups may comprise gold atoms or streptavidin. Gold surfaces can be readily modified to contain reactive sites. For example, a gold surface can be modified to contain an amine-reactive group (N-hydroxl succinimide (NHS)) by, e.g., by soaking the gold substrate in a 1-10 mM solution of succinimidyl alkanedisulfides such as dithiobis-sulfosuccinimidylpropionate (DSP) or dithiobis(succinimidyl undecanoate) (see, e.g., Peelen et al J. Proteome Res. 2006 5:1580-1585 and Storri et al Biosens. Bioelectron. 1998 13: 347-357). Likewise, a gold surface can be modified to contain thiol-reactive groups may be made by linking a gold surface to an amine-terminated SAM, and further modifying the amine groups using sulfo-succinimidyl-4-(N-maleimidomethyl)cyclohexane-1-carboxylate (Sulfo-SMCC) to yield a maleimide-activated surface. Maleimide-activated surfaces are reactive thiol groups and can be used to link to modified nucleic acids that contain thiol- (e.g., cysteine) groups.

Figure 2:
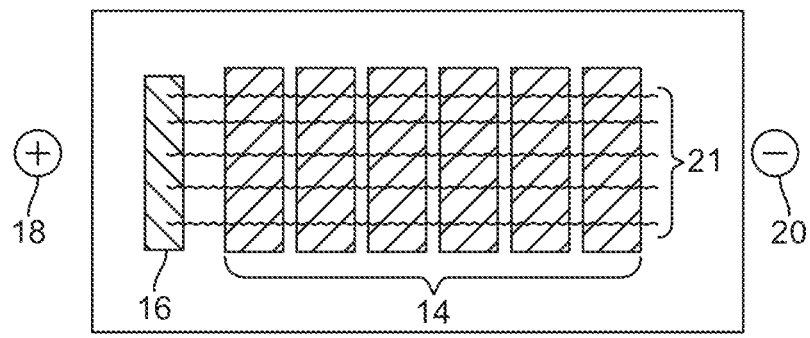
FIG. 2 schematically illustrates a subject nanofluidic device sensing device, shown from the top.

FIG. 2 shows a top down view of the nanofluidic device shown in FIG. 1. The plurality of charge sensors 14, capture area 16 and electrodes 18 and 20 are indicated on FIG. 2. As shown in FIG. 2, the device may be used in conjunction with multiple copies of nucleic acid 21. In use, each copy of nucleic acid 21 is straightened to places a region of interest of the nucleic acid molecule in proximity with a plurality of the charge sensors 14.

Figure 3:
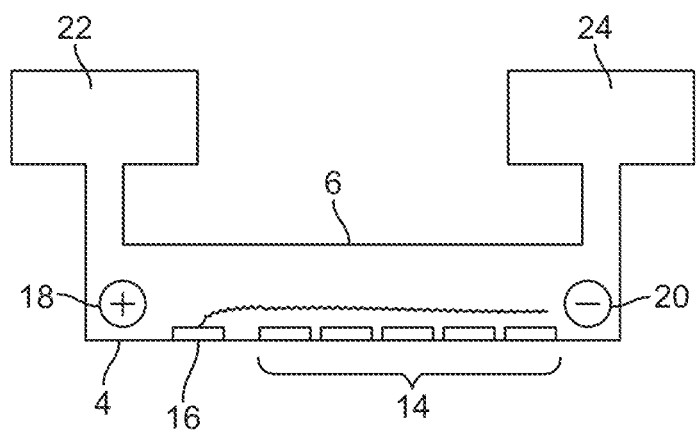
FIG. 3 schematically illustrates a system comprising a subject nanofluidic device sensing device.

A nanofluidic system that comprises a nanofluidic device described above is also provided. As illustrated in FIG. 3, the system may comprise a subject nanofluidic device sensing device (which, as shown, comprises opposing floor 4 and ceiling 6, plurality of charge sensors 14, capture area 16 and electrodes 18 and 20) and a source of reagents 22 that is operably connected to the entrance end of the channel; and a waste line 24 that is operably connected to the exit end of the channel. The source of reagents may comprise sequencing reagents including DNA polymerase, nucleotides (G, A, T and C) and a reaction buffer DNA polymerase, as well as a flushing reagents (e.g., a wash buffer such as $dH_2O$). The various reagents may be different reservoirs, and operably connected to the nanofluidic device via fluid flow path capable of selectively mixing certain reagents together (e.g., polymerase, dG and buffer, polymerase, dA and buffer, polymerase, dT and buffer, or polymerase, dC and buffer, etc.) so that that the desired reagents can be introduced into the entrance of the channel and then flowed through the channel.

A subject device may be fabrication using top-down or bottom-up methods. Top-down methods can be done using photolithograhpy on a bulk substrate. Bottom-up methods, in contrast, starts with atoms or molecules with intrinsic nano-scaled dimension. In one cases, photolithography may be used to define the geometry of channels on a substrate wafer. The geometry is created by several thin-film deposition and etching steps to form trenches. The substrate wafer is then bonded to another wafer to seal the trenches and form channels. Other technologies to fabricate nano-channels include surface micromachining with sacrificial layers, nano-imprinting lithography, and soft-lithography. Bottom up methods may use self-assembled monolayers (SAM). Nano-channels can also be fabricated from the growth of carbon nanotubes (CNT) and quantum wires. Bottom-up methods usually give well-defined shapes with characteristic length about few nanometers. In addition, there are several ways to coat the inner surface with specific charges. Diffusion-limited patterning can be utilized because they can penetrate the entrance of a nanochannel within a certain distance. By introducing several steps of reactants flowing into the nanochannel, it is possible to pattern the surface with different surface charges inside the channel. In one embodiment, a subject device may be fabricated by any suitable method.

A method of analyzing nucleic acid molecules is also provided. In certain embodiments, this method may comprise: anchoring a plurality of identical nucleic acid molecules to the capture area in the above-summarized system, wherein each of the plurality of identical nucleic acid molecules comprises a primer annealed thereto, upstream of the region of interest. The primer may be hybridized to the nucleic acid molecules before or after the nucleic acid molecules are attached to the capture area. Methods for anchoring nucleic acid molecules to a surface are well known and many examples are discussed above. In some embodiments, the identical nucleic acid molecules may have been produced using a primer that has been modified to contain a group that is reactive with or binds to the capture area. In other embodiments, the nucleic acid molecules may be enzymatically modified to contain such a group (e.g., ligated to a functionalized oligonucleotide). Next, the method involves applying an electrophoretic force along the longitudinal axis of the channel using the first and second electrodes. In this step, a voltage differential between the electrodes produces an electric field that induces the free end of the nucleic acid molecules to migrate toward the anode, due to the net negative charge of the sugar-phosphate backbone of the nucleic acid chain, thereby straightening the nucleic acid molecules and placing the region of interest in proximity with a plurality of the charge sensors (see FIG. 1). At this point, after flushing the channel, the method involves taking an initial reading the charge of the straightened nucleic acid molecules using the array of charge sensors. This charge reading may be stored for later analysis. Next, the method involves flowing a DNA polymerase and a nucleotide precursor selected from dA, dG, dC and dT through the channel under primer extension conditions, i.e., conditions by which the primer can be extended by the action of the polymerase if the template contains a complementary nucleotide. After, flushing the channel, the method involves reading the charge of the straightened nucleic acid molecules using the array of charge sensors. Whether the primer has been extended can be determined by comparing the charge measurements obtained before and after the polymerase and nucleotide precursor, etc., have been flowed through the channel. In other words, the charge of the straightened nucleic acid molecule is measured before and after contact with the polymerase and nucleotide precursors, etc. If the charge of the molecule has changed, then a nucleotide has been added to the molecule (onto the nucleic acid chain that is initiated by the primer).

In some embodiments, the method may comprise repeating the flush, charge measurement, extension, flush and charge measurement steps for each of the different nucleotide precursors. If this process is repeated times, the sequence of at least part of the region of interest can be obtained. In some embodiments, the sequence of at least two contiguous nucleotides, e.g., at least 3, 4, 5, 10, 50 or 100, up to 500 or 1,000 contiguous nucleotides) of the region may be determined.

As will be described in greater detail below, the identical nucleic acid molecules used in the method may comprise multiple copies of the region of interest, wherein each of the copies comprises a binding site for the sequencing primer upstream (i.e., so that extension of the primer progresses into the region of interest). As will be described in greater detail below, the identical nucleic acid molecules comprising multiple copies of the region of interest may be made by rolling circle amplification (see, e.g., Lizardi et al, Nat. Genet. 1998 19:225-32) of a set of identical circular templates (e.g., a set of amplicons that have been amplified from a single molecule of nucleic acid and then circularized). In certain embodiments, the primer used for the rolling circle amplification may be functionalized provide an amplification product that can be anchored to the capture area by the end that contains the primer. As will be discussed in greater detail below, the flushing may be done using low ionic strength solution, or diode charge depletion.

An exemplary embodiment is described below. This embodiment enables label free electronic detection of DNA bases as they are incorporated in a sequencing-by-synthesis reaction. This embodiment avoids costly fluorophores required for optical detection and avoids damaging polymerase enzymes by illumination. Compared with other electronic readout technologies, it relies on direct detection of incorporated backbone charge as opposed to ions released into the solution as a byproduct of the DNA replication reaction. Because incorporated backbone charges are fixed above the detector, integration is possible over a longer timescale than is it for mobile charges, which diffuse away. In other words, the nanofluidic device measures final reaction products at equilibrium as opposed to reaction kinetics.

The nanofluidic device comprises a multiplicity of parts, some of which are described here. At the highest level, the device contains an ISFET (Ion Sensitive Field Effect Transistor) array chip integrated with an array of nanofluidic channels. This array of nanofluidic channels is mated with a micro fluidic channel sample and chemical delivery network. In place of the ISFET array may be some other array of charge sensors, and in place of the micro fluidic channel network may be some other construct which delivers biological sample and chemicals to the nanofluidic channel units, however for the purposes of this disclosure we describe an ISFET array and a micro fluidic channel network.

Figure 4:
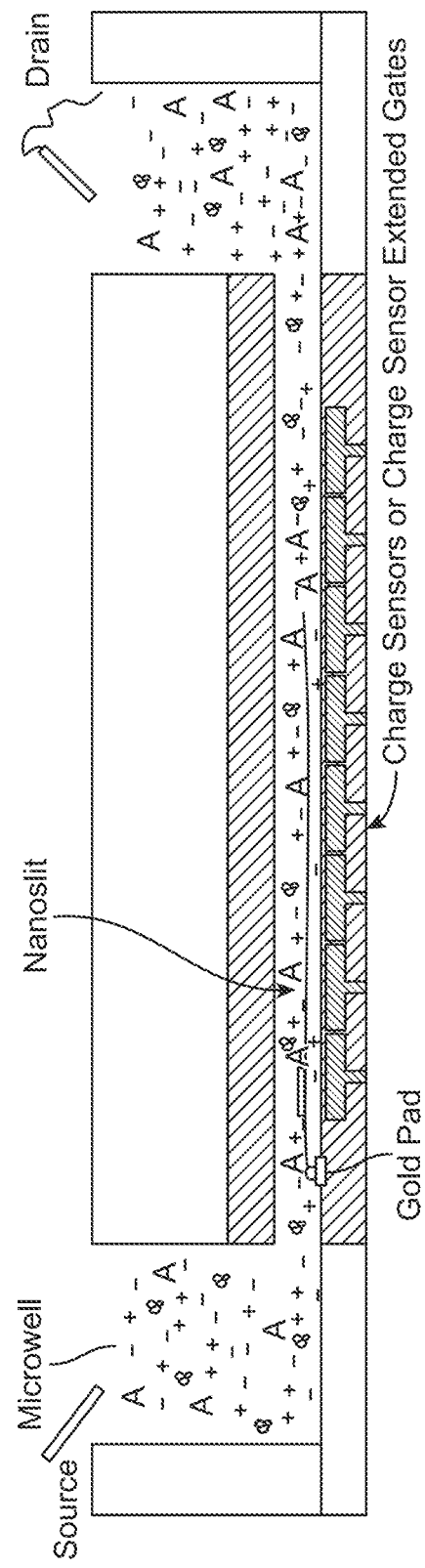
FIG. 4 schematically illustrates a single device containing a nanofluidic channel with integrated charge sensors and two microwells.

The nanofluidic channel devices (an example of which is schematically illustrated in FIG. 4) each contain a multiplicity of integrated ISFET sensors (charge sensors) which may be monitored by the integrated ISFET circuitry during operation of the device. Each nanofluidic channel device may be fluidic connection to the micro fluidic channel network for efficient delivery of DNA, enzymes, primers, other reactants and cofactors, reaction buffers, washing buffers, and other necessary biological and chemical components, and for the efficient removal of reactant by product from the nanochannel unit. The nanofluidic channel in each nanochannel device may be connected to the micro fluidic network through microwells, one at each end of the nanofluidic channel. The nanofluidic channel itself comprises a channel with a critical depth on the order of the Debye screening length, for all practical purposes, this is likely on the order of less than 1 micron, e.g., less than 100 nm and even possibly several tens of nanometers or less.

The depth is important, since the function of the nanochannel is to force the target DNA molecule to reside within close proximity to the integrated charge sensors which reside on the inner surfaces of the nanofluidic cavity, or which reside just under the surfaces of the nanofluidic cavity, or even within the nanofluidic channel itself. Maintaining close proximity between the target DNA molecule and the charge sensors prevents mobile ions in solution from electrically screening the DNA charge and allows for the charge sensors to detect the charge on the DNA backbone.

The nanofluidic channel also contains a capture area i.e., a sticky pad, somewhere on its interior surface which is designed to capture the ends of target DNA molecules as they are introduced into the nanofluidic channel. This sticky pad may comprise gold, for example, which would catch the ends of the DNA molecule if the ends were functionalized with a thiol group. Alternatively, the sticky pad could first capture streptavidin molecules, which could subsequently capture biotin-modified DNA. The sticky pad may comprise any material, solid state, biological or chemical as long as it is chosen in conjunction with the functional groups on the ends of target DNA molecules so that it binds to the ends of the target DNA molecules and nothing else on the target molecule. The purpose of this sticky pad is to immobilize multiple, identical (clonal) DNA molecules at one location in the channel so that when they are later stretched along the channel for sequencing they are physically aligned at the same starting point.

The nanofluidic channel may optionally contain multiple segments with different surface charges. These segments of different surface charges may be present in order to allow nanofluidic diode behavior. It will later be described how nanofluidic diode functionality can be used to reduce free charge carrier concentration in the channel, thus reducing charge based background noise. Note, in certain cases it may also be advantageous to build a step, bend, or curve into the channel such that when the molecule is pulled taught it is pressed more tightly against the surface with embedded sensors.

The nanofluidic device allows for electrical charge based monitoring of incorporated nucleotides during cycle controlled DNA synthesis. One embodiment of the sequencing process flow is as follows:

1) One or more identical clonal DNA strands with functionalized ends are introduced into the nanofluidic channel. As the molecules flow past the sticky pads (gold strips for example) their ends bind, but the remainder of the molecule floats freely in the nanochannel. After a sufficient number of target DNA molecules are anchored by their endpoints in the nanofluidic channel, a primer may be annealed to the DNA strands at this point. In certain cases, the primer may be annealed to the DNA strands prior to their introduction in to the channel.

2) The channel is flushed with de-ionized water, or another low ionic strength solution, causing removal of unbound high molecular weight molecules and small molecules from the channel, including partial removal of salts and ions. Following this bulk fluidic flushing, the channel may optionally be further flushed of charged species by using the "nanofluidic diode charge depletion" procedure described below.

Figure 5:
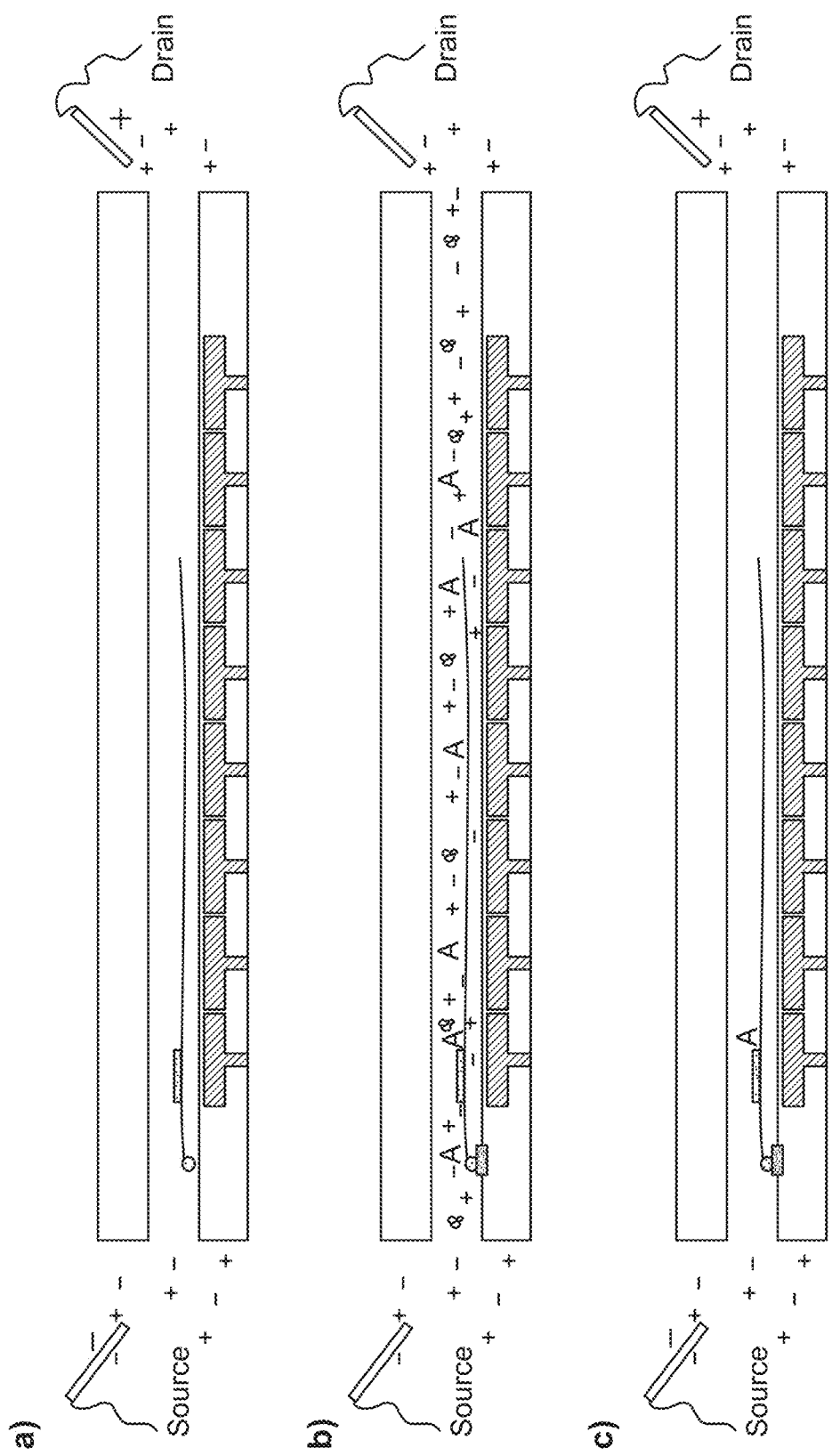
FIG. 5 schematically illustrates a method of sequencing by synthesis in nanochannels by incorporated charge detection. Step a) flush all mobile charge carriers out of channel electrophoretically, then measure total charge above electrodes Step b) flow in polymerases, cofactors and nucleotides. Step c) flush all charge carriers out of channel electrophoretically, then measure total charge above electrodes. Determine difference in total charge before and after the synthesis step.

3) While applying an electrical bias across the ends of the nanochannel (along the axial length) to further elongate the DNA molecule, the charge above each integrated sensor is determined (see FIG. 5).

4) Following the charge quantification measurement, all necessary reactants are flowed into the channel to allow for the possible incorporation of a base type. Reactants include, but are not limited to, DNA polymerases, $Mg^{2+}$ ions, and nucleosides of one type (the precursors to either Adenine, Guanine, Cytosine or Thymine). The polymerization reaction is allowed to proceed to completion, thus allowing for the incorporation of zero, one or multiple bases per reaction site, depending on the target DNA molecule sequence, and the identity of the nucleosides flowed into the nanochannel.

5) Following completion of the incorporation event (multiple bases in a row in the case of a homopolymer segment) the channel is cleared of all reactants and washed (see step two). Step #'s 2, 3, and 4 are repeated in series with a different nucleoside type each time. The cycle might be A, T, C, G, A, T, C, G for example.

Because each incorporated nucleotide carries a charge of ~−1 e, measurement of the number of incorporated charges during each polymerization cycle is equivalent to measuring the number of incorporated bases. Because only one variety of nucleosides is flowed in during each polymerization step, the number, type, and order of incorporated nucleotides can be determined.

The nanofluidic channel in combination with two microwells or nanofluidic delivery channels and the associated buried electrodes can be referred to as a single nanofluidic device. A single nanofluidic device may contain all of the hardware required to perform DNA sequencing on either a single DNA molecule (if the sensitivity allows it) or an ensemble of clonally identical molecules loaded into the channel and anchored to the same anchor point in the same orientation. For the purposes of the sequence information present, this is equivalent to just one molecule. The presence of many copies does not introduce any new sequence into the nanofluidic device, rather it only serves to improve signal to noise relative to measurement of a single molecule.

Thus, the rate of DNA sequencing using such a chip may be calculated if two quantities are known, namely, the number of independent nanofluidic devices present on the chip, and the time elapsed per cycle in the sequencing protocol. Here we assume a 1 inch×1 inch (2.54 mm×2.54 mm) total chip area, which is the largest practical size for CMOS fabrication of an array of ISFETs. If the nanochannel dimensions are set to 1 micron×50 microns, then the number of devices is roughly 125,000. If one assumes a cycle time of 10 sec, and an average number of incorporated bases per molecule per cycle of 1, then 12,500 bases per second of data can be generated. Thus in one hour 45 Mb of data can be generated. From here it would be possible increase the sequencing rate simply by scaling up the number of chips included in each sequencing tool. For instance a 10×10 array of one-square-inch chips would produce 4.5 Gb of data per hour.

For an array of nanofluidic devices large scale integration of electronic interconnects for the buried ISFETs may be required. Additionally large scale integration of the fluidic network would be required to deliver sample, buffers, and reagents to the microwells. This could be accomplished by having a nanofluidic channel network in a layer that sits on top of the nanofluidic device layer. This nanofluidic channel may reside in a bonded PDMS layer, for example. That nanofluidic channel network may be designed with highly branched, interdigitating delivery and waste extraction channels.

Figure 6:
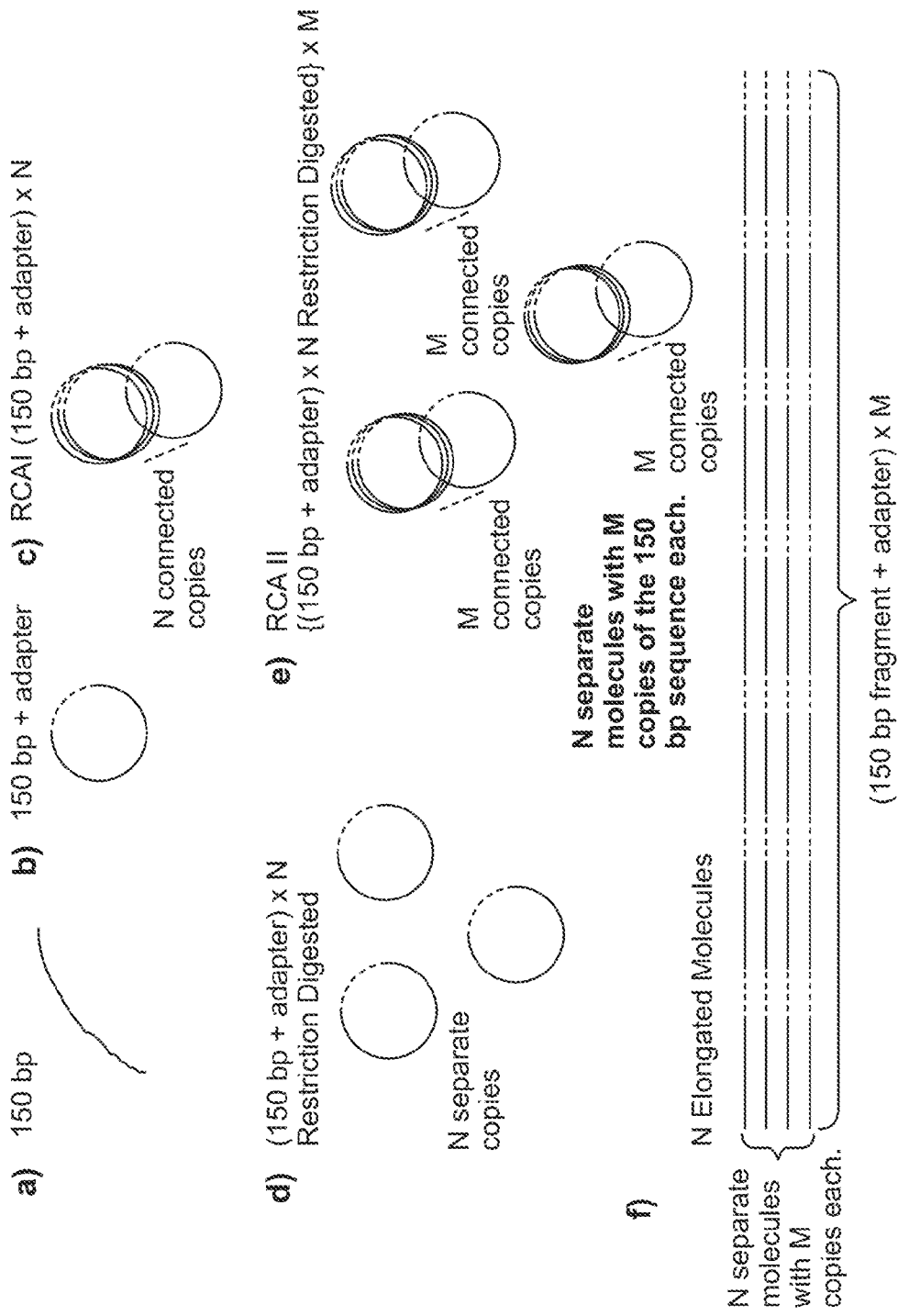
FIG. 6 schematically illustrates a method of circle to circle amplification. Step a) DNA molecules are enriched from a sample using any number of selection strategies (SureSelect for prefiltering, for example) and are then sheared to 150 bp in length. Step b) an RCA (rolling circle amplification) adapter is ligated to the 150 bp target fragments. Step c) Rolling circle amplification generates N copies of the molecule N×(150 bp+adapter segment). Step d) This complex is digested with a restriction enzyme to create N separated circles (150 bp+adapter), each identical to the molecule in (b). Step e) The molecules in (d) are each copied M times using RCA. Step f) N molecules, each with M adapter+150 bp repeat segments are available to be loaded into a nanochannel or nanoslit.

While it should be possible to measure incorporation events from a single target DNA molecule in a nanochannel, it is recognized that multiple clonal copies of a molecule may be required in order to obtain sufficient signal over the electrical background noise (of which there are multiple sources). A sample preparation procedure is shown in FIG. 6 which describes one method of obtaining multiple, clonal concatemers of target DNA molecules. In brief, rolling circle amplification is used to generate a concatemer of copies of a 100 bp to 5 kb, e.g., 100 bp to 500 bp or about 150 mer target sequence. Once complete, this single molecule of many concatemers (1000 for example) is digested into separate fragments by a restriction enzyme. The process of RCA is then run a second time, on the multiple fragments. This procedure is known in the field as circle to circle amplification (F. Dahl et al., PNAS Mar. 30, 2004 vol. 101 no. 13 4548-4553). It could either be performed on the target DNA prior to introduction onto the microfluidic/nanofluidic chip, if an adequate multiplexed sample delivery system were employed (possibly including the use of microbeads for carrying sample to the wells), or Circle to Circle Amplification (C2CA) could be performed in the microwells adjacent to each nanofluidic channel. In the latter case, no more than one 150 mer target molecule would need to be loaded into each nanofluidic well and then all of the reagents and washes required for C2CA would subsequently need to be loaded into each well. Technical challenges exist regardless of the approach, however given knowledge common to the field, several methods exist that could be adapted for delivering multiple clonal concatamer molecules into the microwell of each nanochannel unit.

Figure 7:
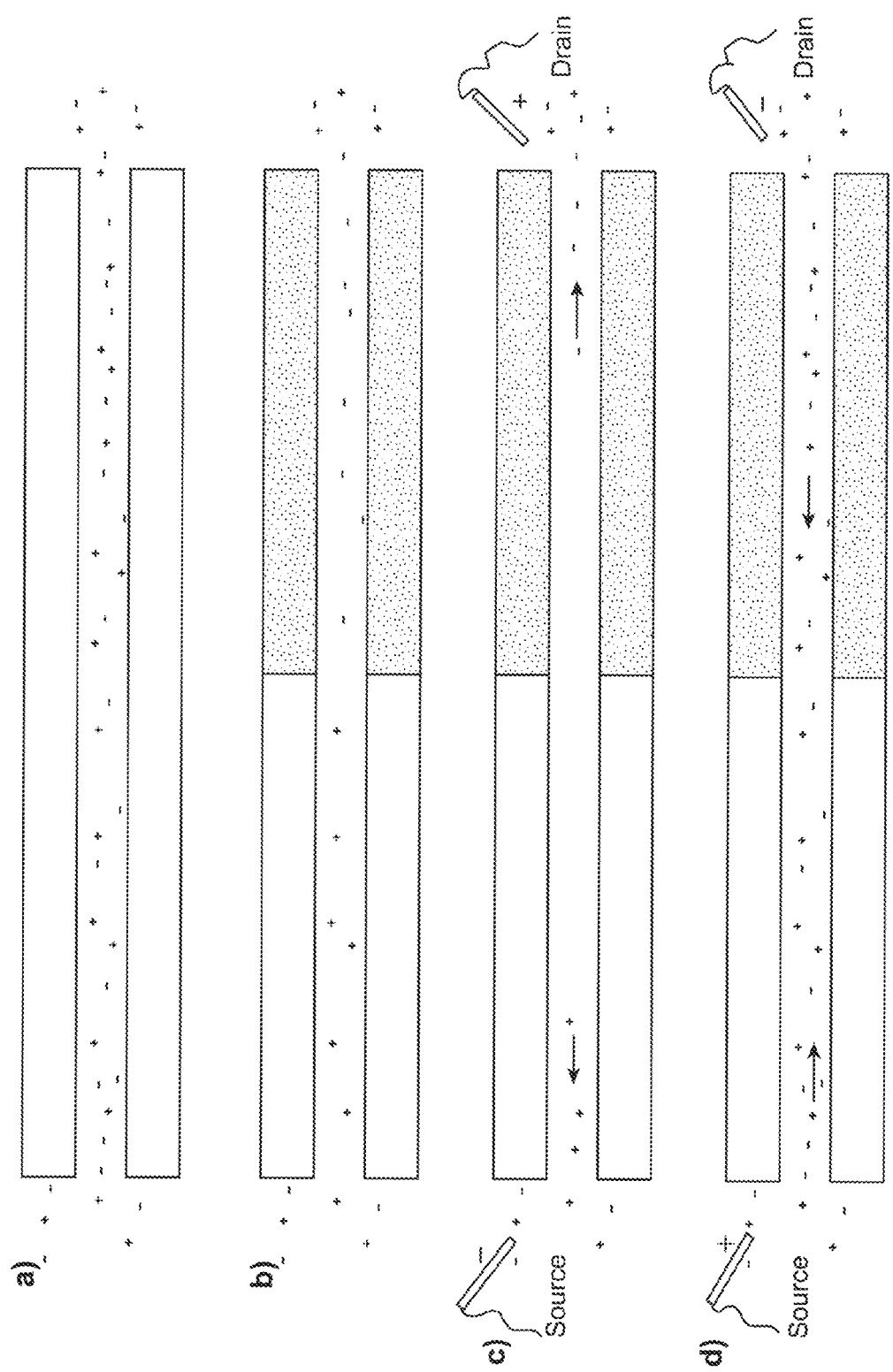
FIG. 7 schematically illustrates: a) a nanofluidic channel with neutral surfaces (zeta potential~0 mV). An equal concentration of positive and negative charge carriers will occupy the nanochannel. b) a nanofluidic channel with two distinct surfaces. The left half has a surface with negative zeta potential, and the right half has a positive zeta potential. As a result, the left half of the nanochannel experiences anion depletion and cation enrichment, whereas the right half of the channel experiences anion enrichment and cation depletion. c) a nanofluidic diode under reverse bias. Charge carriers are driven from both channel segments leaving the entire nanochannel depleted of charge. d) a nanofluidic diode under forward bias. No charge depletion occurs and current can flow continuously through the channel.

During the charge measurement phase of the sequencing cycle, the goal is to determine whether new charges have been incorporated into the DNA backbone as a result of new bases being added. Since there will be a limited number of copies of the target DNA molecule at rest above each electrode in the nanofluidic channel, it is important that any non-DNA charges are flushed out of the channel to reduce the background charge noise. As described above, this could partly be accomplished by flushing the nanofluidic channel with a low ionic strength solution, such as deionized water. As an additional step for purifying the channel from charges, a nanofluidic diode strategy could be used to deplete the channel of mobile charge carriers. Nanofluidic diodes and have been described in other publications, however the use of a nanofluidic diode strategy to deplete a nanochannel of mobile charge carriers for reduction of background noise in the charge detection region has not yet been done. There are several variations of nanofluidic diodes in the literature, however the basic concept can be described simply by choosing just one form, illustrated in FIG. 7. Here a straight, shallow channel (on the order of the Debeye screening length) that has two distinct regions is described (see FIG. 7, panels b-d). The first region of channel has wall surfaces with a highly negative zeta potential and in the second region, wall surfaces have a highly positive zeta potential (see FIG. 7, panel b). The surface charge in the two regions causes enrichment of mobile counter-ions and depletion of mobile co-ions in the fluidic segments contained within two channel regions. This structure, in which two conducting regions of different charge carrier types are placed in direct contact, exhibits diode like behavior when forward and reverse biases are applied across the channel length (see FIG. 7, panels c-d).

Figure 8:
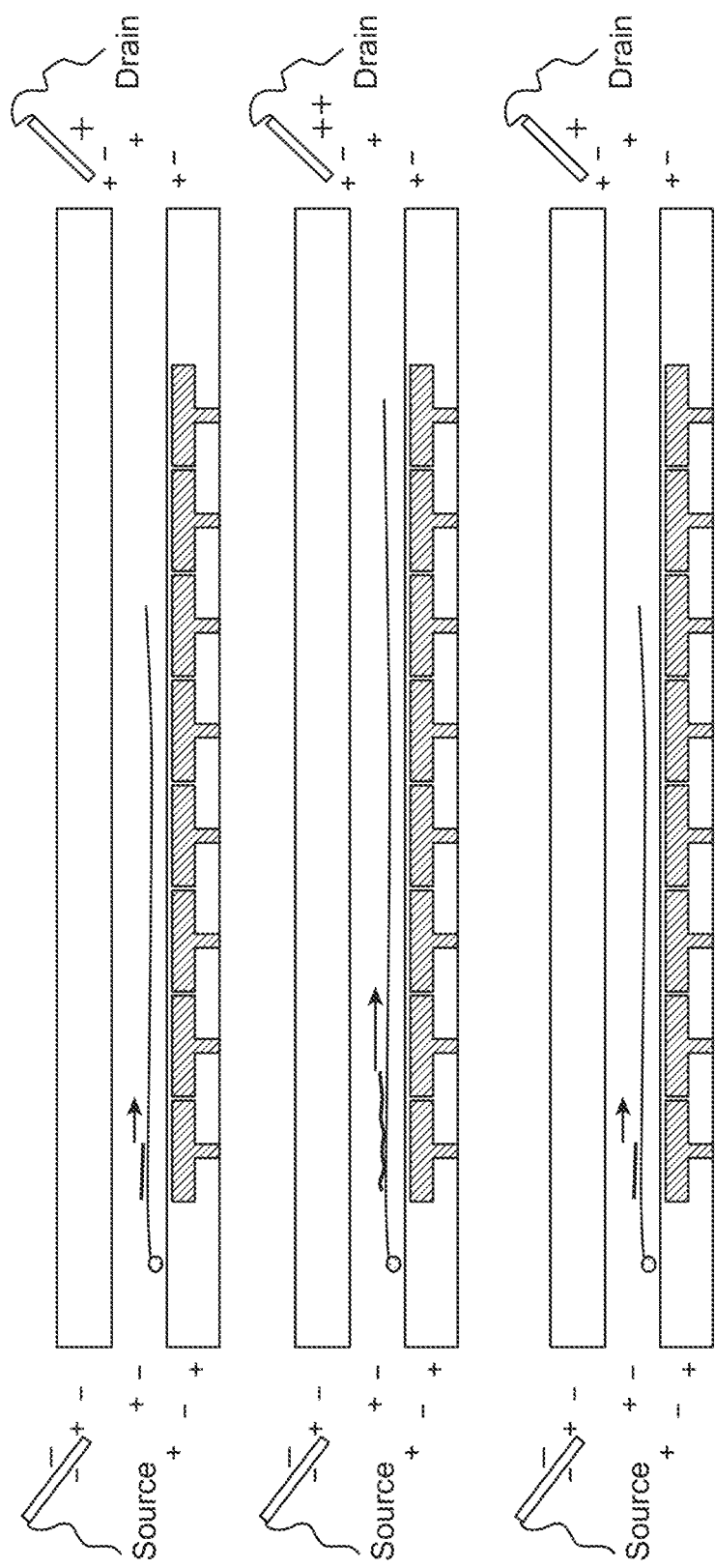
FIG. 8 schematically illustrates a method for controlled molecular stretching and contraction with Locked-in source drain bias AC modulation for a multielectrode measurement.

In the device, a long DNA molecule, covalently fixed to the channel at one end and otherwise floating freely in the channel, is stretched along the axis of the channel by an electric field during measurement phase of the sequencing cycle. In such a state, the DNA molecules, once stretched, resides over a multitude of independently addressable FET gate electrodes, each of which has its own independent sources of noise. If, during the charge measurement phase, a DNA molecule is moved through the channel so that its charge was differentially sampled by the gate electrodes, the effect of FET noise could be somewhat mitigated. While each long DNA molecule will be fixed to the channel surface at one end, DNA is a flexible polymer with spring like properties, and the degree of stretching will depend on a number of factors including nanochannel depth, local ionic strength and applied electric field strength. Applied ionic field strength is a user controlled independent variable, which can be adjusted to modulate the extension length of a molecule in the nanochannel, thus moving segments of the molecule back and forth over more than one electrode in a controlled way, as illustrated in FIG. 8. Whatever frequency this bias modulation is applied at could be locked into during readout of the electrode signals.

Confinement induced elongation of long DNA molecules in nanochannels has been demonstrated (see, e.g., Tegenfeldt 2004 PNAS 101 p 10979; Mannion el. al. 2006

Biophysical Journal 90 p 4538 and Reccius 2005 Physical Review Letters 95 p 268101). The mechanics of molecular stretching (see FIG. 9) are understood, and are not explained in detail in this disclosure. Finally, the framework of Debeye screening length for a polymer in an electrolytic solution is also understood by the field. The following formula describes Debye screening length in an electrolyte:

$$\lambda_D = \frac{1}{\sqrt{4\pi l_B \sum_i \rho_i z_i^2}}$$

Figure 10:
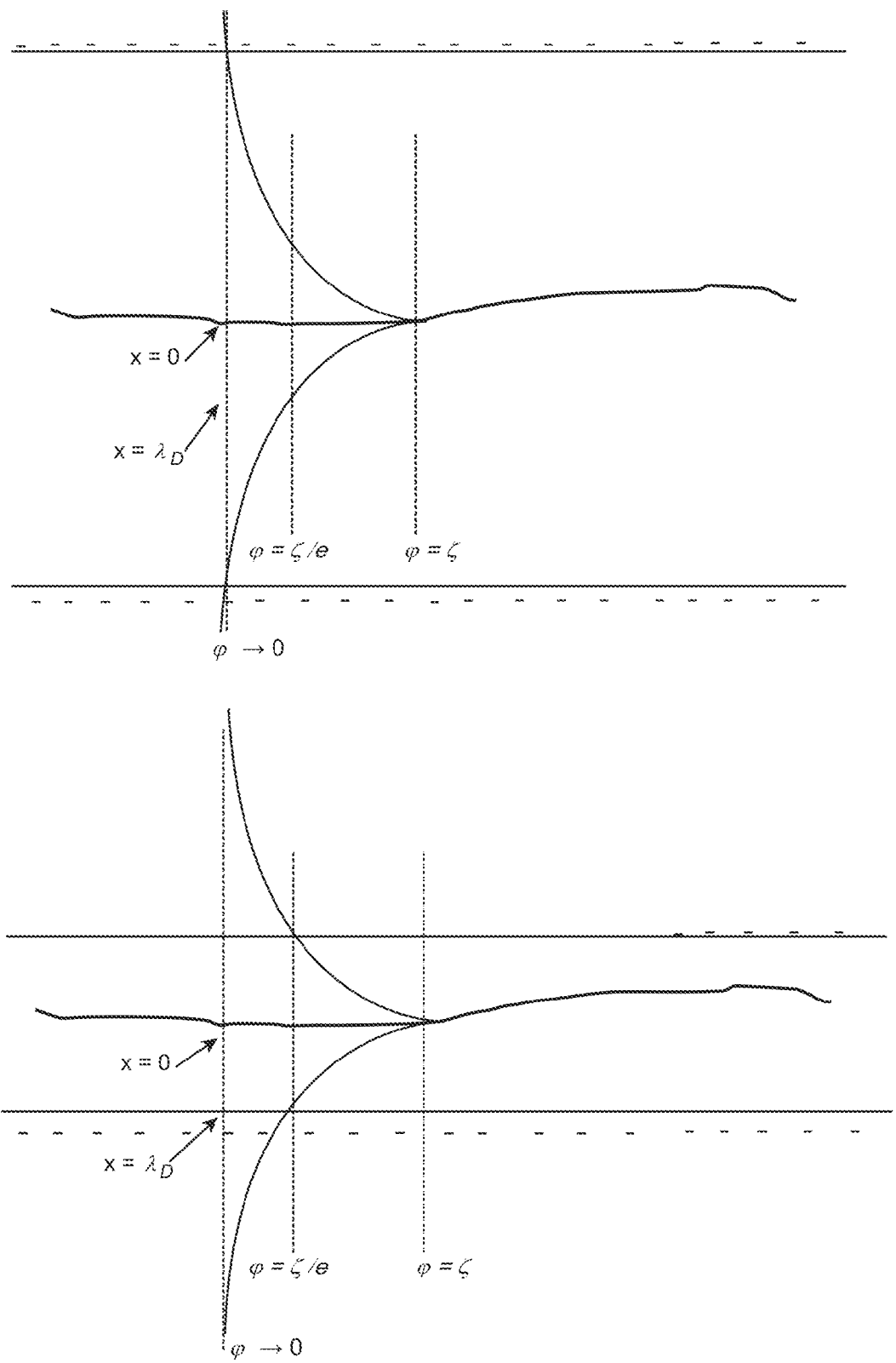
FIG. 10 (Top panel) shows an elongated DNA molecule in a nanofluidic channel which has a depth of greater than twice the Debye screening length. Charge on the DNA molecule's backbone does not perturb the solution potential near the wall since the charge is screened over that distance by ions in solution. The bottom panel of FIG. 10 shows an elongated DNA molecule in a nanofluidic channel which has a half-depth less than the Debye screening length. In this case, it will be possible for a charge sensor located on or just under the channel surface to detect electrical charge on the DNA backbone.

The concept of using the vertical confinement of a nanocavity in conjunction with a low ionic strength buffer to force a charged macromolecule to reside within an ionic screening length distance of the charge detector is illustrated in FIG. 10 and is presented in US20110227558, which is incorporated by reference herein for all purposes.

All publications and patent applications cited in this specification are herein incorporated by reference as if each individual publication or patent application were specifically and individually indicated to be incorporated by reference. The citation of any publication is for its disclosure prior to the filing date and should not be construed as an admission that the present invention is not entitled to antedate such publication by virtue of prior invention.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

Accordingly, the preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

EXEMPLARY EMBODIMENTS

Provided herein is a nanofluidic device sensing device comprising: a) a channel comprising a floor and a ceiling, wherein the floor and the ceiling are spaced by less than 1 μm and the channel comprises an entrance end and an exit end that define the longitudinal axis of the channel; b) an array of charge sensors in the floor and/or ceiling of the channel, arranged along the longitudinal axis of the channel; c) a capture area in the floor and/or ceiling of the channel at the entrance end of the channel, wherein the capture area comprises surface exposed groups that bind to or react with and end of a functionalized nucleic acid molecule; and d) a first electrode and a second electrode, wherein the first and second electrode are positioned to provide an electrophoretic force along the longitudinal axis of the channel, thereby straightening any nucleic acid molecule that is attached to the capture area and placing a region of interest of the nucleic acid in proximity with a plurality of the charge sensors. In any embodiment, the floor and ceiling of the channel may be spaced by less than 100 nm. In any embodiment the channel may be up to 100 μm in length. In any embodiment, the entrance end and an exit end of the channel may be adapted for connection with a source of reagents and a waste line, respectively. In any embodiment, the charge sensors may be ion sensitive field effect transistors. In any embodiment, the channel may be not linear along its longitudinal axis. In any embodiment, the nanofluidic device may comprises at least 10 of the charge sensors. In any embodiment, the charge sensors may be spaced from one another by less than 1 μm. In any embodiment, the surface exposed groups may comprise gold atoms or streptavidin. In any embodiment, the device may comprise a plurality of nanofluidic diodes, wherein the diodes divide the channel into multiple segments with different surface charges.

Also provided is a nanofluidic system comprising: a nanofluidic device sensing device described above; a source of reagents that is operably connected to the entrance end of the channel; and a waste line that is operably connected to the exit end of the channel. In this embodiment, the source of reagents may comprise DNA polymerase, nucleotides and DNA polymerase reaction buffer. In any of these embodiments, the floor and ceiling of the channel may be spaced by less than 100 nm. In any of these embodiments, the channel may be up to 100 μm in length. In any of these embodiments, the entrance end and an exit end of the channel may be adapted for connection with a source of reagents and a waste line, respectively. In any of these embodiments, the charge sensors may be ion sensitive field effect transistors. In any of these embodiments, the channel may be not linear along its longitudinal axis. In any of these embodiments, the nanofluidic device may comprise at least 10 of the charge sensors. In any of these embodiments, the charge sensors may be spaced from one another by less than 1 μm. In any of these embodiments, the surface exposed groups may comprise gold atoms or streptavidin. In any of these embodiments, the channel may comprise a plurality of nanofluidic diodes, wherein the diodes divide the channel into multiple segments with different surface charges.

Also provided is a method of sample analysis comprising: a) anchoring a plurality of identical nucleic acid molecules to the capture area in any embodiment the system described above, wherein each of the plurality of identical nucleic acid molecules comprises a primer annealed thereto, upstream of the region of interest; b) applying an electrophoretic force along the longitudinal axis of the channel using the first and second electrodes, thereby straightening the identical nucleic acid molecules and placing the region of interest in proximity with a plurality of the charge sensors; c) taking an initial reading the charge of the straightened nucleic acid molecules using the array of charge sensors; d) flowing a DNA polymerase and a nucleotide precursor selected from dA, dG, dC and dT through the channel under primer extension conditions; e) reading the charge of the straightened nucleic acid molecules using the array of charge sensors; f) determining whether the primer has been extended by in step d) by comparing the charges obtained before and after the flowing step d). This method may comprise repeating steps d) through f) for each of the different nucleotide precursors. Any embodiment of this method may comprise repeating steps d) through f) for each of the different nucleotides of step d) multiple times, thereby obtaining a sequence for at least part of the region of interest. In any of these embodiments, identical nucleic acid molecules may multiple copies of the region of interest, wherein each of the copies comprises a binding site for the primer upstream therefrom. In this embodiment, the identical nucleic acid molecules comprising multiple copies of the region of interest may be made by rolling circle amplification. In any of these embodiments, the primer used for the rolling circle amplification may be functionalized at the 5' end to provide an amplification product that can be anchored to the capture area by its 5' end. Any of these embodiments may comprise flushing the channel with a low ionic strength solution between steps b) and c) and between d) and e). Any of these embodiments may comprise flushing the channel of charged species by diode charge depletion.

What is claimed is:

1. A nanofluidic sensing device comprising:
    a) a channel comprising a floor and a ceiling, wherein said floor and said ceiling are spaced by less than 1 µm and the channel comprises an entrance end and an exit end that define the longitudinal axis of said channel;
    b) an array of charge sensors in the floor and/or ceiling of said channel, arranged along the longitudinal axis of said channel;
    c) a capture area in the floor and/or ceiling of said channel at the entrance end of said channel, wherein said capture area comprises surface exposed groups that affix an end of a functionalized nucleic acid molecule to the capture area; and
    d) a first electrode and a second electrode, wherein said first and second electrodes are positioned to provide an electrophoretic force along the longitudinal axis of said channel, thereby straightening any nucleic acid molecule that is attached to said capture area and placing a region of interest of said nucleic acid molecule in proximity with a plurality of said charge sensors.

2. The nanofluidic device of claim 1, wherein the floor and ceiling of said channel are spaced by less than 100 nm.

3. The nanofluidic device of claim 1, wherein said channel is up to 100 µm in length.

4. The nanofluidic device of claim 1, wherein the entrance end and an exit end of said channel are adapted for connection with a source of reagents and a waste line, respectively.

5. The nanofluidic device of claim 1, wherein said charge sensors are ion sensitive field effect transistors.

6. The nanofluidic device of claim 1, wherein said channel is not linear along its longitudinal axis.

7. The nanofluidic device of claim 1, wherein said nanofluidic device comprises at least 10 of said charge sensors.

8. The nanofluidic device of claim 1, wherein said charge sensors are spaced from one another by less than 1 µm.

9. The nanofluidic device of claim 1, wherein said surface exposed groups comprise gold atoms or streptavidin.

10. The nanofluidic device of claim 1, wherein said channel comprises:
    a plurality of distinct regions that are in direct contact with one another and that comprise different surface charges, wherein at least one region has a wall surface that provides a negative zeta potential, and at least one region has a wall surface that provides a positive zeta potential, wherein the different surface charges in the distinct regions cause:
    enrichment of mobile counter-ions and depletion of mobile co-ions in the fluidic regions contained within the distinct channel regions; and
    diode-like behavior of the channel when forward and reverse biases are applied across the channel length.

11. A nanofluidic system comprising:
    a nanofluidic sensing device comprising:
    a) a channel comprising a floor and a ceiling, wherein said floor and said ceiling are spaced by less than 1 µm and the channel comprises an entrance end and an exit end that define the longitudinal axis of said channel;
    b) an array of charge sensors in the floor and/or ceiling of said channel, arranged along the longitudinal axis of said channel;
    c) a capture area in the floor and/or ceiling of said channel at the entrance end of said channel, wherein said capture area comprises surface exposed groups that affix an end of a functionalized nucleic acid molecule to the capture area; and
    d) a first electrode and a second electrode, wherein said first and second electrodes are positioned to provide an electrophoretic force along the longitudinal axis of said channel, thereby straightening any nucleic acid molecule that is attached to said capture area and placing a region of interest of said nucleic acid molecule in proximity with a plurality of said charge sensors;
    e) a source of reagents that is operably connected to the entrance end of said channel; and
    f) a waste line that is operably connected to the exit end of said channel.

12. The nanofluidic system of claim 11, wherein the source of reagents comprises:
    DNA polymerase, nucleotides and DNA polymerase reaction buffer.

* * * * *

UNITED STATES PATENT AND TRADEMARK OFFICE
CERTIFICATE OF CORRECTION

PATENT NO. : 9,683,958 B2
APPLICATION NO. : 14/482803
DATED : June 20, 2017
INVENTOR(S) : John Mannion et al.

It is certified that error appears in the above-identified patent and that said Letters Patent is hereby corrected as shown below:

On the Title Page

In item (56), in Column 2, under "Foreign Patent Documents", Line 1, delete "W02010044932" and insert -- WO2010044932 --, therefor.

In the Specification

In Column 1, Line 56, before "Step" insert -- . --.

In Column 4, Line 54, delete "sulfhydrl" and insert -- sulfhydryl --, therefor.

In Column 4, Line 61, delete "hydroxl succinimide" and insert -- hydroxysuccinimide --, therefor.

In Column 5, Line 33, delete "that that" and insert -- that --, therefor.

In Column 5, Line 38, delete "photolithograhpy" and insert -- photolithography --, therefor.

In Column 7, Line 17, delete "Sensistive" and insert -- Sensitive --, therefor.

In Column 10, Line 7, delete "concatamer" and insert -- concatemer --, therefor.

In Column 10, Line 29, delete "Debeye" and insert -- Debye --, therefor.

In Column 11, Line 4, delete "Debeye" and insert -- Debye --, therefor.

In the Claims

In Column 14, Line 24, in Claim 11, delete "comprising:" and insert -- comprising; --, therefor.

Signed and Sealed this
Twentieth Day of February, 2018

Andrei Iancu
*Director of the United States Patent and Trademark Office*